(12) United States Patent
Hughes et al.

(10) Patent No.: US 8,363,861 B2
(45) Date of Patent: Jan. 29, 2013

(54) ENTERTAINMENT SYSTEM FOR USE DURING THE OPERATION OF A MAGNETIC RESONANCE IMAGING DEVICE

(75) Inventors: Brian Hughes, Calabasas, CA (US); Ryan A. Hughes, Calabasas, CA (US)

(73) Assignee: Brian Hughes, Calabasas, CA (US)

( * ) Notice: Subject to any disclaimer, the term of this patent is extended or adjusted under 35 U.S.C. 154(b) by 452 days.

(21) Appl. No.: 12/724,937

(22) Filed: Mar. 16, 2010

(65) Prior Publication Data

US 2010/0238362 A1  Sep. 23, 2010

Related U.S. Application Data

(60) Provisional application No. 61/161,971, filed on Mar. 20, 2009.

(51) Int. Cl.
*H04R 25/00* (2006.01)

(52) U.S. Cl. ............ 381/189; 348/61; 600/411; 381/124

(58) Field of Classification Search ........................ None
See application file for complete search history.

(56) References Cited

U.S. PATENT DOCUMENTS

| | | | |
|---|---|---|---|
| 3,601,667 A * | 8/1971 | Desmond et al. ............. | 257/671 |
| 4,901,141 A | 2/1990 | Costello | |
| 5,076,275 A | 12/1991 | Bechor et al. | |
| 5,134,373 A | 7/1992 | Tsuruno et al. | |
| 5,277,184 A * | 1/1994 | Messana ...................... | 600/421 |
| 5,412,419 A * | 5/1995 | Ziarati .......................... | 348/61 |
| 5,414,459 A | 5/1995 | Bullwinkel | |
| 5,577,504 A | 11/1996 | Salloway et al. | |
| 5,627,902 A | 5/1997 | Ziarati | |
| 5,861,865 A | 1/1999 | Anand et al. | |

(Continued)

FOREIGN PATENT DOCUMENTS

| DE | 20021037924 | 3/2004 |
|---|---|---|
| JP | 2002102203 A | 4/2002 |

(Continued)

OTHER PUBLICATIONS iPod shuffle (2nd generation)—Technical Specifications, Web page printout from www.apple.com website—http://support.apple.com/kb/SP27, last modified Oct. 13, 2008.*

(Continued)

*Primary Examiner* — Greg C Bengzon
(74) *Attorney, Agent, or Firm* — Dobrusin & Thennisch PC

(57) ABSTRACT

An entertainment system for use with a magnetic resonance imaging (MRI) device that includes video glasses and headphones. A Faraday shield encloses the entertainment system to reduce adequately RF signals from entering or leaving the entertainment system. The entertainment system may have non-ferromagnetic RF low-pass filters between parts of the system, such as the control unit and the video glasses, to reduce higher RF signals from entering or leaving those parts. To replace the battery and or entertainment media, a person opens the entertainment system's Faraday shield when not MRI imaging or outside the MRI magnet room. The door has an Faraday shield overlapping the system Faraday shield and making low resistance RF contact. The entertainment system has a minimal amount of ferromagnetic material so that it may operate within the high magnetic field of the MRI magnet bore with minimal performance degradation. The entertainment system uses non-ferromagnetic speakers in the headphone. Passive ear protection and noise cancellation reduce the loud noise of the MRI system heard by the patient to a level where the patient can hear the entertainment. The entertainment system includes a charger for the rechargeable batteries.

20 Claims, 6 Drawing Sheets

U.S. PATENT DOCUMENTS

| | | | |
|---|---|---|---|
| 5,864,331 | A | 1/1999 | Anand et al. |
| 5,877,732 | A | 3/1999 | Zimmer |
| 6,188,015 | B1* | 2/2001 | Curran et al. ............... 174/353 |
| 6,421,235 | B2* | 7/2002 | Ditzik ....................... 361/679.3 |
| 6,463,316 | B1 | 10/2002 | Brungart |
| 6,483,719 | B1* | 11/2002 | Bachman .................... 361/816 |
| 6,674,652 | B2* | 1/2004 | Forte et al. .................. 361/800 |
| 6,686,539 | B2* | 2/2004 | Farquhar et al. ............. 174/525 |
| 6,774,929 | B1* | 8/2004 | Kopp ............................. 348/61 |
| 6,930,891 | B1* | 8/2005 | Hama et al. .................. 361/800 |
| 7,353,041 | B2* | 4/2008 | Zhu et al. .................. 455/550.1 |
| 7,550,679 | B1* | 6/2009 | Wershoven ................... 174/377 |
| 7,623,360 | B2* | 11/2009 | English et al. ............... 361/816 |
| 7,697,281 | B2* | 4/2010 | Dabov et al. ............ 361/679.55 |
| 8,085,942 | B2* | 12/2011 | Rasmussen .................. 381/71.1 |
| 8,180,077 | B1* | 5/2012 | Slaughter ..................... 381/189 |
| 2005/0024820 | A1* | 2/2005 | Chen et al. .................... 361/686 |
| 2005/0257370 | A1* | 11/2005 | Cunningham et al. .......... 29/840 |
| 2007/0030646 | A1* | 2/2007 | Hsu ............................... 361/687 |
| 2009/0093705 | A1* | 4/2009 | Vangdal ........................ 600/410 |
| 2009/0147462 | A1* | 6/2009 | Zhu et al. ................. 361/679.31 |
| 2010/0231483 | A1* | 9/2010 | Bazih et al. ....................... 345/8 |
| 2010/0234722 | A1* | 9/2010 | Trcka et al. ................... 600/410 |
| 2010/0277877 | A1* | 11/2010 | Dinh et al. ..................... 361/749 |
| 2011/0090626 | A1* | 4/2011 | Hoellwarth et al. ..... 361/679.01 |
| 2012/0013525 | A1* | 1/2012 | Trcka et al. ........................ 345/8 |

FOREIGN PATENT DOCUMENTS

| | | |
|---|---|---|
| WO | 2005119284 | 12/2005 |
| WO | 2006132542 | 12/2006 |

OTHER PUBLICATIONS

Electromagnetic Scattering by Píergiorgío Uslengbi, New York, San Francisco, London, 1978.

NMR, A Persepetive on Imaging by General Electric, Manibir Singh, Sep. 2002.

Electromagnetic Analysis and Design in Magnet Resonance Imaging by Jianming Jin, 1962, Library of Congress Cataloging in Publication Data.

Micro-loopless Antenna for High Resolution MR Imaging of the Brain Warren Grundfest, BME 298, Fall 2003.

John F. Schenck, "The role of magnetic susceptibility in magnetic resonance imaging: MRI magnetic compatibility of first and second kinds", Med. Phys. 23 (6), Jun. 1996.

Search Report and Written Opinion for PCT/US2010/027994 mailed Oct. 20, 2010 (Related PCT application).

IPRP PCT/US2010/027994 mailed Sep. 29, 2011 (Related PCT application).

* cited by examiner

ENTERTAINMENT SYSTEM FOR USE DURING THE OPERATION OF A MAGNETIC RESONANCE IMAGING DEVICE

CLAIM OF PRIORITY

This application claims priority from U.S. Provisional Application 61/161,971, filed Mar. 20, 2009, incorporated herein by reference.

FIELD OF THE INVENTION

The present invention relates to methods and devices for the entertainment of a patient during the operation of a magnetic resonance imaging device generally.

BACKGROUND OF THE INVENTION

In the medical field, magnetic resonance imaging (MRI) is a commonly used non-invasive technique to diagnose the medical condition of a patient. Typically, the MRI system operator places the patient within the central bore of large homogeneous magnetic field and the MRI system subjects the patient to a set of gradient magnetic fields and RF pulses. The MRI system measures the very small RF signals emitted from nuclei in the patient, and processes the information to reconstruct an image of the part of the patient's body in the MRI system. The images produced by the MRI have very small amplitude RF signal in the frequency range 50 to 150 MHz. The frequency depends on the strong fix magnetic field and the magnetic gradient fields.

The MRI magnet bore is small, especially in the head-coil, and induces claustrophobic feelings in many patients. The MRI system produces loud noises as the MRI system changes the gradient magnetic fields. These loud noises add to the anxiety and discomfort of the patient. Under these conditions, up to 20% of patients do not remain sufficiently still during the 20 to 60 minute process for a successful MRI image. As is known in the art, the MRI system operator may reduce or eliminate the patient's claustrophobic feelings and anxiety by providing the patient with some type of entertainment. The entertainment system calms the patient, distracts the patient from the MRI procedure, and results in more patients remaining sufficiently still during the MRI procedure for adequate image quality.

There are at least six critical areas that must be addressed when providing a patient with some type of entertainment in a MRI system. First, the strong fields generated by the MRI device must not prevent the normal operation of an entertainment system or cause the entertainment system to move in the MRI system's large magnetic field. Second, the large RF pulses from the MRI system must not harm or heat up the entertainment system. Third, the entertainment system must not emit sufficient RF energy to degrade the MRI image quality. Fourth, the Faraday shield used to contain the entertainment system's RF signals must not produce anomalies in the MRI image. Fifth, the entertainment system must fit within the MRI system and comfortably accommodate a wide range of patients. Sixth, the entertainment system must be affordable, reliable, and easy to use.

These critical areas also include competing considerations. It is appreciated that to address one critical area may detract from the performance of another critical area so that the results are not predictable especially when addressing two or more critical areas as discussed herein. Despite these constraints, inventors have designed many types of entertainment systems in an attempt to provide the patient with some entertainment. However, these attempts have failed to provide a self-contained entertainment system that is integrally used within an MRI during the operation thereof as in the present invention.

Features of prior art entertainment system that had little or no use in an MRI due to difficulties associated therewith include but are not limited a battery, video media, storage mediums, various electronics from computers, or otherwise, or combinations thereof. For example, the prior art generally taught that batteries may not operate safely in an MRI, because the eddy current may heat and discharge the batteries. It is appreciated that for an entertainment system to be truly self-contained, the entertainment system may be configured to read data from a storage medium (e.g., a memory card) and process the data into video signals. Such process of data, generally requires processing millions of data with critical time and voltages. It is appreciated that the large magnetic field produced by the MRI may undesirably affect electrical circuits, such magneto resistance, and hall-effect voltages. As such, the prior art provides insufficient teachings that storage mediums such as a memory card and/or the corresponding circuits to read the data and create video signal may be operable in the high magnetic field of a MRI. However, the present invention attempts to solve these problems and others by providing a self-contained entertainments system.

Exemplary entertainments systems include: U.S. Pat. No. 4,901,141 to Costello discloses video systems that supplied video images through optic fibers to the patient. U.S. Pat. No. 5,134,373 to Tsuruno et al. supplies images via optical transfer means from a screen. U.S. Pat. No. 5,861,865 to Anand et al. generates images on LCD displays outside the magnet, which the patients see with mirrors and prisms. These systems retrofit the MRI system with the optical fibers or optical transfer scheme, which is rather expensive to install. The long length of fiber from the MRI control room to the MRI system attenuates the image and degrades the image quality. U.S. Pat. No. 5,076,275 to Bechor et al. generates an image behind the MRI device and has a mirror for reflecting the image to the patient. These systems do not readily accommodate different positions of the patient. The patient is still aware of the surrounding MRI system with these entertainment systems; thus, the systems may not adequately distract the patient. In addition, the lighting in the MRI magnet room can make the display more difficult to watch.

These entertainment systems require expensive installations in the MRI magnet room and bring the entertainment signal through the MRI magnet room Faraday shield. All entertainment systems that bring in the signal by cables have the potential problem of snagging and damaging the long cables. Many patients wear glasses to correct their vision. Typically, the patient cannot wear his or her glasses in the MRI system because the glasses contain ferromagnetic material, such as steel screws. Many of the systems described in prior art do not allow for optical correction.

U.S. Pat. No. 5,412,419, U.S. Pat. No. 5,627,902, and U.S. Pat. No. 6,463,316 disclose bringing the audio to the patient pneumatically through flexible pipes. Long lengths of pipe to bring an audio signal from outside degrade the audio signal quality by attenuating the high frequency audio signal. U.S. Pat. No. 5,877,732 discloses generating the audio with piezoelectric speakers and bringing the audio to the patient with a short length of pipe. U.S. Pat. No. 5,577,504 to Salloway et al. discloses an entertainment system that includes noise cancellation and non-ferromagnetic headphones.

Prior entertainment systems for use in an MRI system are complicated because they transmit the entertainment media from the MRI control room to the MRI magnet room via penetration of the room shielding. These prior entertainment systems require modification to standard, pre-existing MRI facilities. These MRI facilities modifications are expensive and stop operation of the MRI facilities during modification.

Portable video players are much less expensive than the custom entertainment system developed in prior art for use with an MRI system. Portable video players require no costly installation at the MRI facility. These consumer portable video players are the desired affordable self-contained entertainment systems. However, these consumer portable video players may be unsuitable for use in a MRI system because they contain ferromagnetic materials, they emit RF energy that can interfere with a MRI image quality, they may be affected by the RF pulse of a MRI system, they may not be securely attached to the user allowing their use in any position, or otherwise.

Thus, the present invention provides a self-contained, portable entertainment system for use by a patient within a magnetic bore of an MRI device during the operation thereof, wherein the entertainment system at least assists in overcoming one of the aforementioned drawbacks or other drawbacks.

It is appreciated that various entertainment system designs have been provided in U.S. Pat. Nos. 5,134,373, 5,412,419, 5,414,459, 5,577,504, 5,627,902, 5,861,865, 5,864,331, 5,877,732, 5,076,275, 6,463,316, 6,774,929, 4,901,141; International Patent Applications WO2006132542, WO2005119284, JP2002102203A, and DE20021037924; and Published References "Electromagnetic Scattering" by Piergiorgio Uslenghi, "NMR, A perspective on imaging" by General Electric, "Electromagnetic Analysis and Design in Magnetic Resonance Imaging" by Jianming Jin, and "Microloopless Antenna for High Resolution MR Imaging of the Brain" by Warren Grundfest, which are herein incorporated by reference for all purposes.

SUMMARY OF THE INVENTION

An object of the present invention is a portable video player with video glasses and headphones, which a patient wears in the strong magnetic field of an MRI system to calm and entertain the patient. With more patients calm and remaining still during their MRI procedure, MRI system productivity may increase. The present invention's video glasses reduce patient anxiety when inside the small magnet bore of the MRI system. The present invention's headphones reduce the loud noise from the MRI system and allow the patient to hear audio entertainment. Another objective of the present invention is an entertainment system that requires no installation at the MRI facility. The present invention is battery powered and worn by the patient. Another objective of the present invention is a lower cost entertainment system for patients in a MRI system. Another objective of the present invention is downloading (e.g., by way of purchasing or otherwise) the entertainment (e.g., media) either directly (e.g., WiFi, or otherwise) or by transferring (e.g., from a computer or otherwise) to the storage medium (e.g., memory card) of the entertainment system for playing in the entertainment system. The present invention is based on lower-cost, commercially available, consumer entertainment systems.

In the present invention, the patient holds the entertainment system's control unit (e.g., video control unit) in his or her hand and adjusts volume, plays or pauses the entertainment, or turns the entertainment system on or off. The control unit contains a battery for powering the system all day. The control unit contains a replaceable memory card that stores the entertainment. The control unit reads the entertainment from the memory card, generates the video and audio entertainment signals, and amplifies the entertainment signals. A short shielded cable connects the control unit and video glasses. Two very short cables connect the headphone earpieces to the video glasses.

In the present invention, the video glasses have LCD displays and lenses in front of each of the patient's eyes. A printed circuit board in the control unit regulates the LCD displays, and converts the signal from the control unit into imaging signals for the LCD displays. The patient inserts corrective lenses between the LCD display and the patient's eyes for optical corrections. The video glasses enclose the patient's face, eliminating the visual distraction of the MRI magnet bore. Padding at the edge of the video glasses provides a comfortable fit on the patient's face. Adjustable headphone arms connect the headphones to the video glasses and hold the video glasses on the patient's face in front of the patient's eyes.

In the present invention, the entertainment system headphones have sufficient passive noise attenuation to reduce the MRI system noise significantly. In addition, the entertainment system headphones have optional active noise cancellation to further reduce the MRI system noise. The entertainment system headphones have non-magnetic speakers, which generate the audio entertainment. Pads at the edges of the headphones reduce noise getting to the patient ears, and the pads make the headphones more comfortable for the patient. Adjustable headphone arms connect the headphones to the video glasses and hold the headphones firmly against the patient's ears.

In the present invention, a Faraday shield encloses the entire electronics of the entertainment system. The Faraday shield enables the entertainment system to operate in the MRI system. The Faraday shield reduces the RF emission from the entertainment system sufficiently so that the emissions do not significantly degrade with the MRI image quality. The Faraday shield reduces the MRI system pulses from entering the entertainment system and significantly degrading the entertainment or damaging the entertainment system. The control unit, video glasses, and headphone electronics are inside conductive shields. Shielded cables connect these three shields together. Typical Faraday shielding, such as solid metal and metal braiding around a cable, a control unit, a user interface, a video component, an audio component, a storage medium, or otherwise, or any combination thereof may not be suitable in a MRI environment during the operation thereof because they may include too much metal content which may result in anomalies in the MRI images and heating from eddy current as discussed herein. As such, Faraday shielding formed of a conductive metal mesh provides reduced metal content, which may be desirable. The design carefully minimizes the amount of metal in order to minimize anomalies in the MRI images and heating from eddy current that may be caused by dense volumes (e.g., large volumes) of metal material. However, too fine of a metal mesh (low gage wire and/or larger openings between the wires) may form a brittle shielding that may break upon being deformed. For example, a Faraday shielding layer around a cable may crack with flexing, thereby rendering emitting RF signals to or from the cable, which may be form undesirable MRI artifacts and/or eddy currents. Furthermore, using a thicker metal mesh may also by undesirable because of the additional metal content, which may result in MRI anomalies/artifacts. One novel solution to overcome the unpredictable balance between flexibility/rigidity and the amount of metal content in the Faraday shielding is to utilize multiple layers of mesh separated by an insulating layer to resist any contact by the mesh layer. Multiple layers of the mesh provide the rigidity to withstand deformation while isolating each mesh layer from one another to reduce anomalies in the MRI images and/or reduce heating from eddy currents relative to a single mesh or fewer mesh layer having a similar mesh configuration and a similar amount of metal content (e.g., volume). Insulation around the cables protects patients against potential local heating. The insulation also reduces kinking of the cables and potential damage that may result from kinking.

A self-contained portable entertainment system requires one or more doors for replacing the battery and entertainment. The entertainment can be replaced by exchanging the entertainment media or downloading new entertainment to the system by cable or wirelessly. Forming a door that seals the Faraday shield adequately was very difficult and required several experiments to find an adequate solution. One novel solution is to dispose the mesh on the door to overlap significantly and contact the control unit chassis mesh. The novel solution requires low RF resistance between the door mesh and the control unit chassis mesh.

The control unit needs buttons for controlling volume or start/stopping the entertainment. The moving buttons must not allow RF to leak. One novel solution is for the one or more sheets of mesh over the buttons, which connect electrically to the control unit chassis mesh, while still permitting the mechanical button outside the mesh to turn on the electrical buttons inside the mesh by the mesh flexing.

Mesh shielding may not be desirable for shielding over components that require visual communication. For example, mesh across a viewing screen such as a monitor or TV viewing screen or a viewing lens such lens form glasses or LCD-lens may degrade the image quality. One novel solution to shield across a lens such as a LCD-lens unit is to provide an optically transparent conductive film, which does not significantly degrade the LCD image. For example, a transparent conductive film may be used to adequately shield the RF signals while increasing visual image quality relative to a mesh (e.g., metal mesh) material for use across a viewing lens/screen as a Faraday shield in an MRI environment. After careful grounding, the transparent conductive film provided a sufficient Faraday shield for the integral entertainment in a MRI during the operation thereof. Low pass RF filters, before each cable connection, further reduce RF energy from entering or leaving the entertainment system.

The present invention replaces all components found in consumer-electronics entertainment systems that have significant ferromagnetic content, which may prevent the entertainment system from operating properly in the strong magnetic field of a MRI magnet bore.

In the present invention, the MRI system operator replaces the entertainment for different patients, replaces sanitary covers (e.g., when included) on the entertainment system and replaces batteries as needed, while outside the MRI magnet room. The patient selects the entertainment, which are typically movies or TV shows that are stored on solid-state memory cards. The patient adjusts and tests the entertainment system before entering the MRI magnet room. The patient is then ready to more efficiently and more calmly undergo an MRI procedure. At the end of the day, the MRI system operator recharges the large capacity batteries of the entertainment system.

DESCRIPTION OF THE INVENTION

Figure 1:
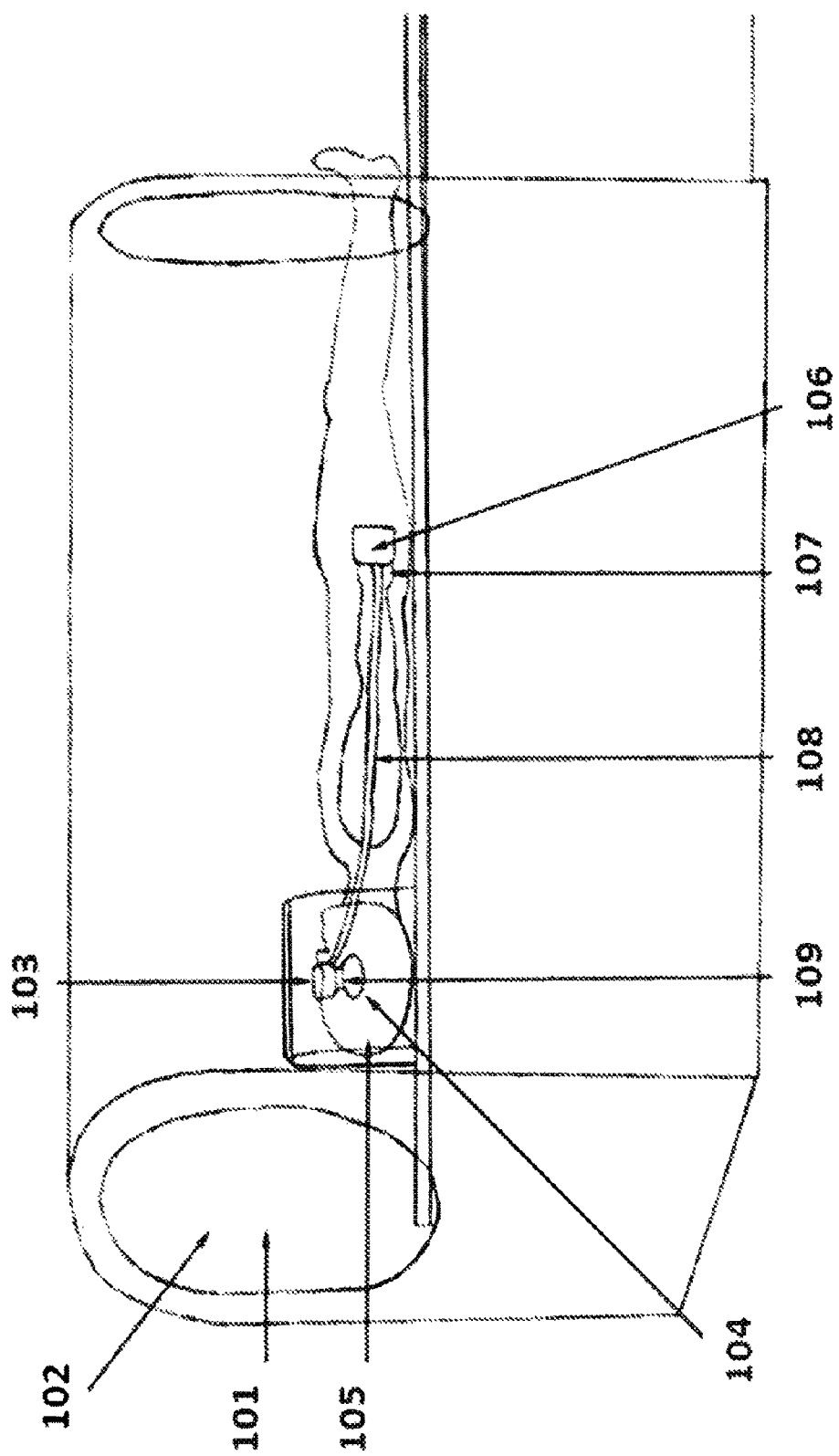
FIG. 1 is a side view of a patient within the magnet bore of MRI system who is wearing the self-contained entertainment system.

The present invention is predicated upon methods and devices for entertaining a patient during the operation of a magnetic resonance imaging (MRI). Referring to the drawings, this is achieved through the use of a self-contained entertainment system 100. As shown in FIG. 1, a patient 101 is positioned within a magnet bore 102 of the MRI. The entertainment system includes a video component such as video glasses 103 and an audio component such as headphones 104 mounted to the patient's head 105. The entertainment system further includes a control unit 106 for controlling (e.g., driving) the video and/or audio components. It should be appreciated that because of the limited amount of space within the magnetic bore, the patient may have limited or no movement that would allow a hand of the patient to be easily moved to or near the head of the patient during MRI imaging. As such, in one embodiment, the control unit 106 may be positioned generally near the patient's hand 107 for interaction therewith. The video glasses 103 display entertainment images (e.g., photos, videos, or otherwise) in front of the patient's eyes to assist in distracting the patient from the MRI environment. The headphones 104 generate audio entertainment near the patient's ears to assist in distracting the patient from the MRI environment. In one embodiment, the headphones 104 may significantly attenuate the audio noise being emitted by the MRI system. In one configuration, the patient may manually control the entertainment system using a user interface, which may be located with the control unit 106.

Figure 2:
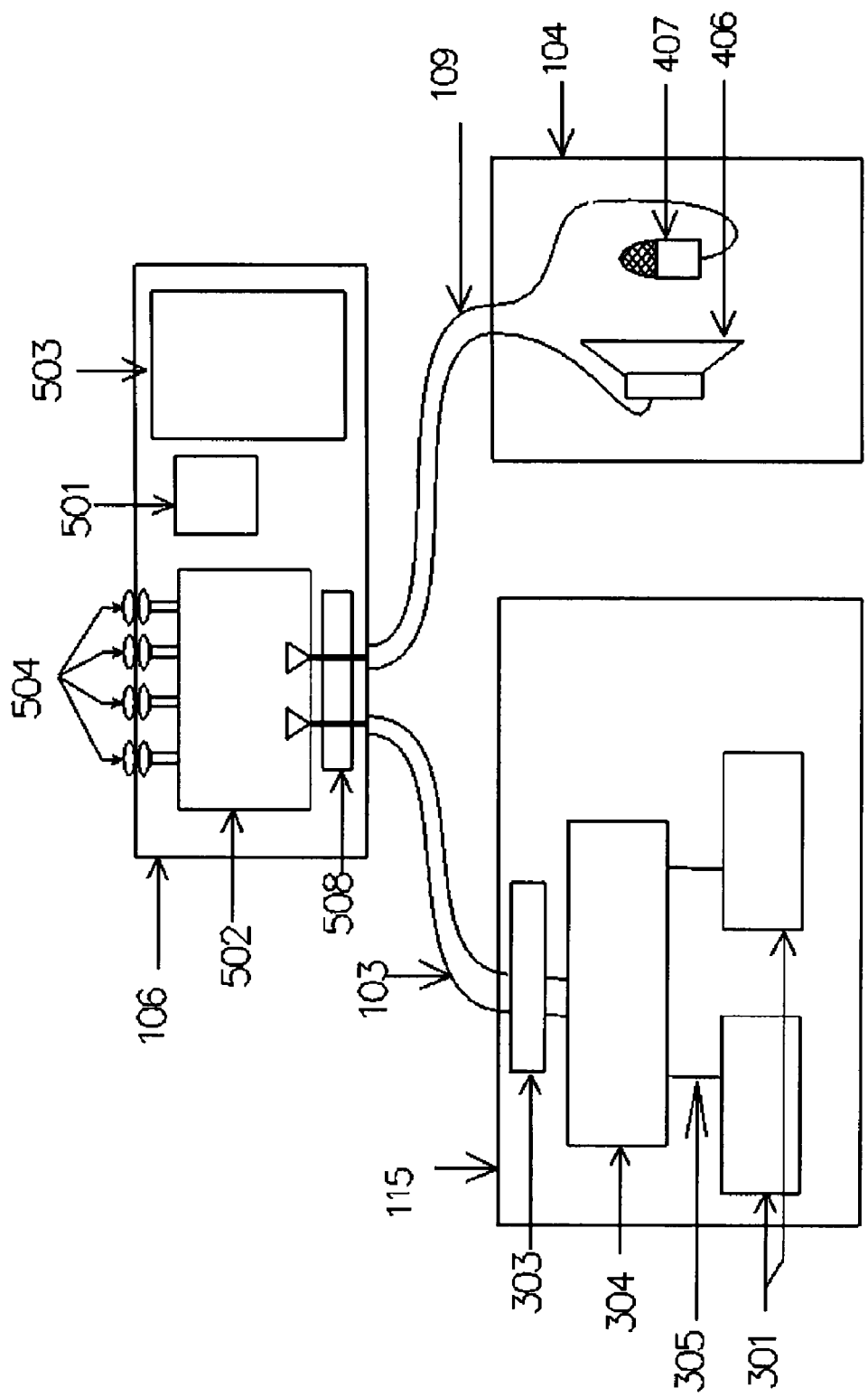
FIG. 2 is a block diagram of one embodiment of the entertainment system according to the present invention.

The entertainment system is preferably an integral device that is also a portable device. Desirably, the entertainment system may not require any installation to the MRI device and/or facilities. For example, the entertainment system is preferably free of wired communication to the MRI, the MRI control room, or both. A block diagram of a non-limiting embodiment of the present invention is shown in FIG. 2. The entertainment system includes (i) the control unit 106, (ii) video component 103, and (iii) audio component 104. Cables 108 connect the control unit 106 to video component 103. Cables 109 connect the video component and audio component 104.

The entertainment system may be configured to substantially reduce or eliminate system noise of the MRI with both passive attenuation and active noise reduction.

The entertainment system may further include one or more shielding layers such as a Faraday shield that at least partially or completely encloses one or more components (e.g., the electronics) of the entertainment system to reduce radio frequency (RF) energy from being emitted from and/or entering the entertainment system. By limiting or eliminating RF energy through the use of the one or more shield layers around the entertainment system, the MRI image quality may be maintained within the acceptable standards. It is appreciated that the one or more shield layers may also protect the entertainment system from the large RF pulses being emitted from the MRI system.

The cables 108 and 109 may also include a shielding layer at least partially or completely encasing the wire(s) extending therethrough. The shielding layer of the cables 108, 109 may extend to interconnect the shielding layer(s) (e.g., 308, 408, 505, or otherwise) that encase the components (e.g., video glasses, headphones, control unit, or otherwise) of the entertainment system.

It is believed that the strong RF pulse of the MRI may induce eddy currents in metals, which may produce artifacts in the MRI images such as shadowing and blurring artifacts. When formed, the RF induced eddy currents decay with time to become either resistive heating (e.g., localized heating) or re-emitted at RF signals. As such, it is appreciated that the shield layer may be further configured to substantially resist or eliminate the formation of eddy current artifacts. It is contemplated that the formation of eddy currents may increase as the volume of metal increases such as in solid metal components. Therefore, it is desirable that the shielding layer(s) provides a decrease in volume of solid metal. In one preferred embodiment, the shielding layer(s) is formed of a conductive metal mesh so that the formation of eddy currents (e.g., eddy current artifacts) may substantially be reduced (e.g., attenuated) or eliminated relative a similarly shaped shielding layer formed of solid metal thereby optimizing conflicting requirements of a Faraday shield to provide high RF signal attenuation while reducing eddy currents small enough to prevent MRI image anomalies or heating.

The shielding layer (e.g., Faraday shield) may be formed as mesh instead of a solid conductor, provided the mesh size may be smaller than the wavelength of the RF signal. The shielding lay may be further configured to substantially reduce or prevent RF signals from being emitted or from entering the entertainment system. Filters such as meshes, screens, or otherwise may be utilized to reduce the requirements on the shielding layer in certain configurations of components for the entertainment system. Desirably, the shielding layer attenuates the RF signals by an amount greater than about 65 dB at frequencies less than about 300 MHz. The preferred embodiment should adequately attenuate the RF signal without creating significant heating and artifacts.

In a preferred configuration, the shielding layer is formed of metal (such as shim stock or otherwise) due to its flexibility (e.g. elasticity) and high strength for resisting plastic deformation. Examples of suitable metal materials include copper, silver, gold, brass, Rhodium, Iridium, Platinum, Titanium, other metallic materials, the like or otherwise. Of course other specific materials are available such as non-metallic conductors, including graphite, solutions of salts, and all plasmas and/or those commonly used in electronics or otherwise. As previously gleaned upon, a fine metallic mesh may not be suitable for cables because the mesh may crack (e.g., break, stretch, or otherwise) from repeated or acute flexing (e.g., bending or deforming) that may result in undesirable RF signal leaking. Suitable material (mesh type and dimensions) and their combinations with insulating layers for this MRI application are discussed herein. It is appreciated that after a system failure (e.g., crack in the Faraday Shield that results in undesirable RF signal leaking, the mesh may be soldered at critical joint(s) (e.g., cracks) to provide an adequately repaired Faraday shield. In one specific non-limiting example, the entertainment system includes multiple shielding layers of metallic screen material (e.g., 100 mesh copper screen (e.g., 100 wires per inch) soldered together at the joints). Exemplary wire strengthening materials include materials sold under product Copper Shielding Cloth 100 Mesh, which are commercially available from Screen Technology Group, Inc., Washougal, Wash.

It is appreciated the number of shielding layers (e.g., mesh layers) may be from about 1 to about 5 layers (e.g., 2 layers of copper mesh having 100 wires per inch) so that the entertainment system may be sufficiently RF shielded while substantial reducing or eliminating the formation of eddy current artifacts in the MRI images.

The shielding layer includes a plurality of openings therein. The openings may be geometrical or non-geometrical (i.e. irregular) in shape. The geometry of the openings may vary depending upon the needs of a given application. Available shapes of the openings include circular, triangular, square or rectangular, hexagonal, octagonal, etc, or otherwise.

Also the size of the openings may vary for each application. It is contemplated that the openings includes a diameter less than 5 mm, 2 mm, 0.5 mm, 0.25 mm, 0.1 mm or smaller. Also, it is contemplated that the average diameter may be from about 0.1 mm to about 1 mm, or otherwise. It should be appreciated that the shape and size of the openings may vary throughout the shielding layer. However, in one preferred configuration the shape and size of the openings are consistent throughout the shielding layer.

The diameter of the threads or wires forming the first component may also vary for each application. It is contemplated that the thread or wires includes a diameter less than 10 mm, 5 mm, 2 mm, 0.5, or 0.25 mm or smaller. Also, it is contemplated that the average diameter of the threads or wires may be between 0.05 mm to 2 mm, between 0.075 mm to 1 mm, between 0.1 and 0.8 or otherwise. It should be appreciated that the shape and size of the wires may vary throughout the shielding layer. However, in one preferred configuration the shape and size of the wires are consistent throughout the shielding layer. Also, the cross-sectional shape of the wires may be circular, elliptical, square, rectangular, heptagon, hexagon, or otherwise.

The number of threads (e.g., wires) may vary for each application. It is contemplated that the number of threads (e.g., thread count) may include about 5, 25, 50, 75, 100, 150, 200, or more strands/inch. Examples of suitable number of strands include between about 15 to about 200 strands/inch or from about 50 to about 150 strands/inch, or otherwise. To substantially resist or prevent a single point of failure in the shielding layer, multiple shielding layers may be used. However, it is contemplated that multiple opposing shielding layers, when included, may result in the formation of eddy currents from direct contact between the shielding layers. The entertainment system may further include at one least spacer layer between opposing shielding layers to further reduce the metal density, to resist any displacement that would bring the two opposing shielding layers into direct contact with each other, or both. In one preferred embodiment, the spacer layer includes an insulating layer. The insulating layer may include a thickness of less than about 0.25 mm, typically less than about 0.127 mm, and more typically less than about 0.025 mm. The insulating layer (e.g., a polyimide insulating layer) may include a dielectric strength of at least about 500 volts, typically at least about 1000 volts, and more typically at least about 5000 volts (e.g., about 7000 volts). The insulating layer may be formed of a rigid material. However, in one preferred embodiment, the insulating layer may be a flexible insulating layer. In such embodiments, the insulating layer may be composed, for example, of polymers (e.g., thermoplastics such as polyimides, polyamides, polycarbonate, polyethylene, polypropylene, polybutylene, polystyrene, polyurethane, vinyl, or any combination thereof), or other materials. Exemplary insulating materials include materials sold under the product designation 1 Mil KAPTON® Tape—RoHS Compliant, which are commercially available from Kapton Tape, Torrance, Calif. As discussed herein, the combination of multiple layers of mesh shielding with a insulating layer therebetween provides a solution to minimizing metal content while maintaining rigidity/pliability sufficiently to provide high RF signal attenuation and reduce eddy currents small enough to prevent MRI image anomalies or heating.

It should be appreciated that the shielding layer(s) (e.g., Faraday shield) may be integrally formed with at least a portion of a housing (e.g., control unit, cables, video component such as the video glasses, audio component such as the headphones, or any combination thereof). For example, the material utilized for forming the housing (e.g., plastic material or otherwise) may further include conductive material, such as a conductive metal or conductive form of carbon (e.g., copper, nickel, carbon nano tubes, or otherwise) so that the housing is "loaded" with the conductive material throughout. As such, the "loaded" housing may be configured to reduce or eliminate the formation of eddy currents as discussed herein. Another example, patterned conductive layer on the surface of the housing, (e.g., a metal film, conductive paint, or otherwise). In this arrangement, the shielding integrated in the housing may replace the one or more shielding layers. However, it is appreciated that the shielding integrated in the housing may be provided separately (e.g., in addition to) the shielding layer (e.g., mesh, transparent film, or otherwise) to reduce or eliminate the formation of eddy currents. In this arrangement, the shielding layer may be separate from and secured to (e.g., adhesively bonded, soldered, or otherwise) the housing (e.g., of the control unit, the video component, the audio component, cables, or otherwise, or any combination thereof).

The entertainment system may include one or more cables having one or more wires for interconnecting the various components for providing communication and/or power therebetween. A cable 108 connects the control unit 106 and the video glasses 103 together. The cable 108 may be at least about 1 foot in length; however, typically, the cable 108 may range from about 1 to about 15 feet or from about 2 to about 5 feet in length. Cables 109 connect each earpiece of the headphones 104 to the video glasses 103. The cables 109 may be at least about 1 inch in length, however typically the cables range from about 1 to about 12 inches or from about 2 to about 6 inches in length.

The cables further include at least one shielding layer that at least partially or completely encases the wire(s) therebetween. It is contemplated that the shielding layer (e.g., metallic mesh) in cables may be susceptible to cracking when sharply bent or kinked, which may result in a crack in the shield that may reduce the integrity of the shielding layer. In one preferred embodiment, cable 108 includes at least two shielding layers that are generally opposing one another (e.g., stacked) with an insulating layer therebetween as discussed herein. The shielding layers (e.g., two shielding layers of mesh such as copper) form a channel through which the wires extend between the control unit and the video glasses. The shielding layers may substantially reduce or prevent RF signals from being emitted by or from entering the cable 108 while optionally providing rigidity to the cable to reduce kinking thereof. The cable(s) may further include an additional (e.g., second) insulation layer surrounding the shielding layer(s) to protect patients from potential local heating, to reduce kinking, or both of the cable. Exemplary types of material for second insulation layer may include but are not limited to: silicone (e.g., gel), polyurethane (PU) foam, polymers having high melting point as a solid or foam, or otherwise). The second insulation layer may be at least about ⅛ inch thick; however, the insulation may be between about ⅛ and about 1 inch thick or about ¼ to about ¾ inch thick around the shielding layer(s), wires, or both.

The entertainment system may further include at least one low pass filter positioned before the cable interface to the control unit, video glasses, headphones, or any combination thereof to substantially reduce or prevent RF signals from passing through the low pass filter. For example, the low pass filter may be configured to allow low-frequency signals to pass through the low pass filter and/or attenuates (reduces the amplitude of) signals with frequencies higher than the cutoff frequency. Preferably, each cable interface includes the low pass filter. In the preferred embodiment, the cutoff frequency for the low pass filter frequency may be at least about 2 mega hertz (MHz). Therefore, frequencies less than about 2 MHz entering the low pass filter will pass therethrough (e.g., from the control unit, video glasses, or headphones to the respective cable), while frequencies greater than about 2 MHz entering the low pass filter will be attenuated by more than 20 dB prior to passing therethrough (e.g., from the control unit, video glasses, or headphones to the respective cable). The connection cables 108 and 109 may be susceptible to receiving and emitting RF energy, therefore, the low pass filters substantially reduce or eliminate RF energy from entering or being emitting from the components of the entertainment system.

For example, in one non-limiting example, the cables between units (e.g., control unit, video component, audio component, or otherwise) may have the potential of both picking up and transmitting RF signal. Low-pass filters at the ends of each cable allows the electrical signal (e.g., video and audio signals) into and out of the cable with minimal attenuation, (e.g. less than about 10 dB and preferably less than about 6 dB at frequencies less than 1 MHz). The low pass filter may significantly reduce the amplitude of signal in the frequency range of about 50 MHz to about 150 MHz from entering or leaving the control unit and/or video glasses and/or headphones. In one embodiment, the low-pass filter attenuation in the frequency range of about 50 MHz to about 150 MHz may be at least 20 dB. It is believed that a typical single pole low pass filter attenuation may increase 20 dB for an increase in frequency of a decade. In one preferred embodiment, the low-pass filter may include a 3 dB attenuation frequency that ranges from about 0.5 MHz to about 5 MHz.

The entertainment system may further include one or more inductors and/or chokes that provide inductance values (e.g., about 50 micro-Henries to about 1,000 micro-Henries) needed for the operation of the entertainment system and/or to substantially reduce or prevent RF signals from being emitted by the power source or through the cables (e.g., wires) in communication therewith. Preferably, the inductor and/or choke is free of ferromagnetic material, iron, or nickel material, or both. In one non-limiting example, the entertainment system may include a plurality (e.g. 3 or more) of non-ferromagnetic inductors applied in series so that the inductance values (e.g., about 50 micro-Henries to about 1,000 micro-Henries) needed by the entertainment circuits are produced with available non-ferromagnetic inductors.

The magnetic fields inside today's MRI magnetic bores may typically range from 1.5 to 3.0 Tesla. Ferromagnetic components are subject to a strong pull in the very large magnetic field of the MRI system. Furthermore, ferromagnetic components may introduce anomalies in MRI images. As such, the components of the entertainment system must have limited or no Ferromagnetism. MRI safety recommendations effectively say that the magnetic force on a component within an MRI bore during the operation thereof should be less than gravity. As such, the magnetic force on the entertainment system should be much less than gravity for comfortable use. The amount of ferromagnetic material may be present in an amount less than about 50 gram (for a magnetic field of about 3.0 Tesla), less than about 20 grams (for a Magnetic field of about 1.5 Tesla), or less than about 10 grams (for a magnetic field of about 0.68 Tesla). For example, a ratio of an allowable amount of ferromagnetic material relative to a magnetic field of the MRI magnetic bore may be less than about 15:1, and typically less than about 10:1. Preferably, the entertainment system may be free of ferromagnetic material. More particularly, the entertainment system may include less than about 15 g/Tesla (grams of ferromagnetic material in the entertainment system per Tesla of the magnetic field in the MRI), preferably less than 10 g/Tesla, or more preferably the entertainment system is free of ferromagnetic material. It was not obvious that we could find non-ferromagnetic components to replace all the components containing ferromagnetic material in an entertainment system.

It should be appreciated that the entertainment system of the present invention may include an oscillator that generates a frequency of less than about 50 MHz (e.g., 47 MHz), and preferably less than about 45 MHz. Optionally, or as an alternative, the entertainment system may include an oscillator that generates a frequency of greater than about 150 MHz, and preferably greater than about 155 MHz. For example, the entertainment system may include an oscillator that does not generate a frequency between about 50 MHz and 150 MHz. Harmonics from entertainment oscillators will produce RF signals that may produce MRI image artifacts. It is believed that harmonics from a simple non-linearity decrease is inversely proportional to frequency squared, (e.g. the RF signal decreases at 20 dB per decade increase in frequency). As such, the shielding layer(s) may be configured to adequately attenuate these harmonic signals such that RF signals by may be reduced by at least about 20 dB per decade increase in frequency. For example, the shielding layer may be configured to reduce RF signals by at least about 20 dB at frequencies between about 50 MHz and about 150 MHz. Furthermore, it is appreciated that the shielding layer may be configured to reduce RF signal less than about 60 dB at frequencies less than about 1 MHz.

Video Glasses

Figure 3:
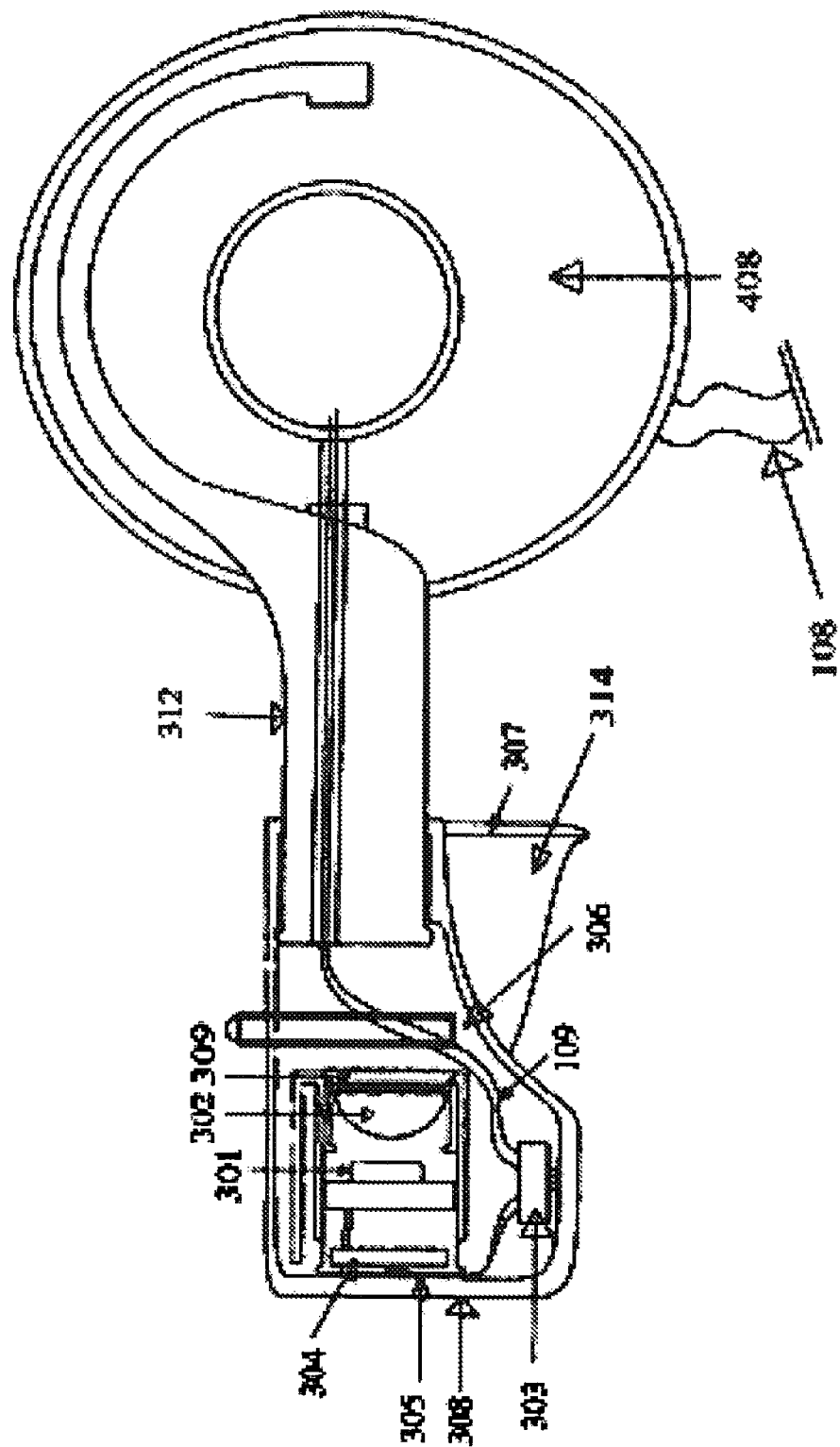
FIG. 3 is a side view of another embodiment of the entertainment system according to the present invention.
Figure 4:
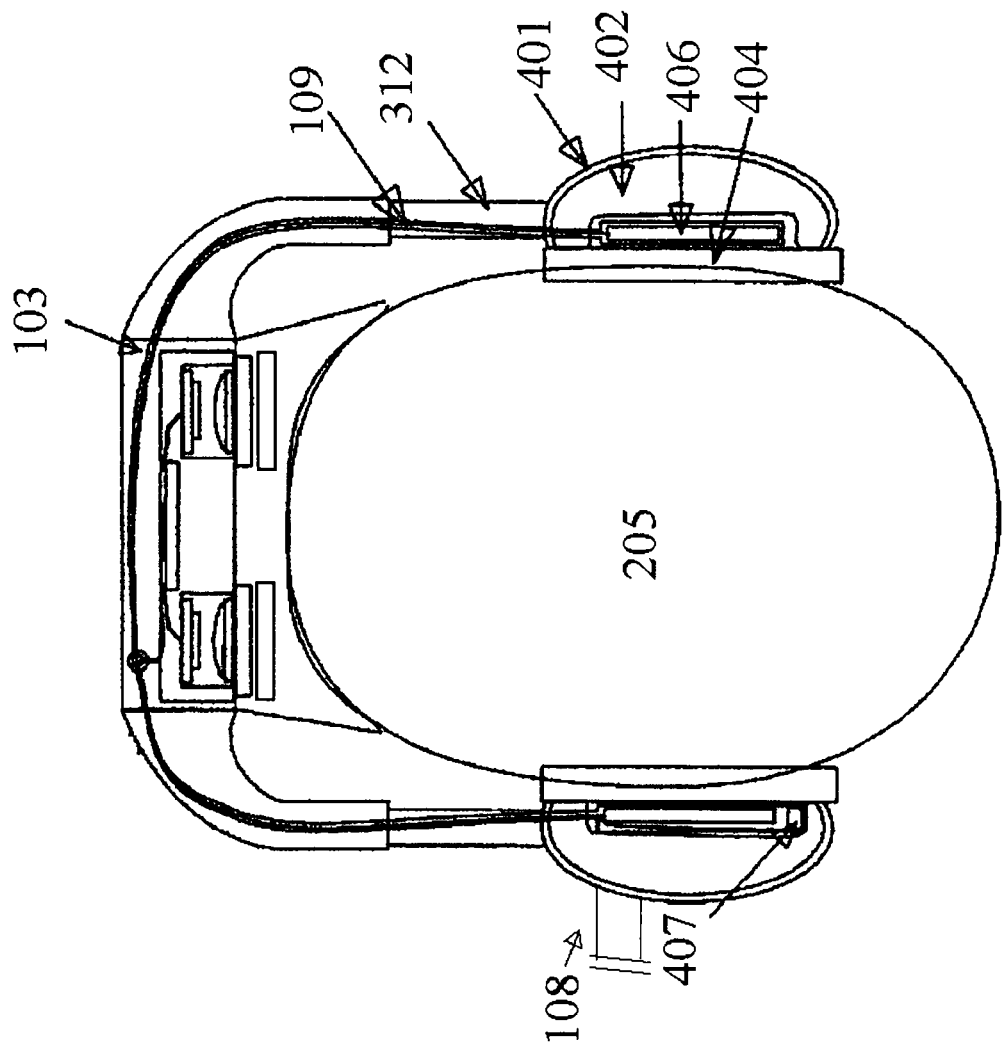
FIG. 4 is a top view of another embodiment of the entertainment system positioned on the head of a patient.

The present invention includes a video component for displaying images to a patient positioned in an MRI during the operation thereof. In one preferred embodiment, the video component may be located in video glasses 103 as shown in FIG. 3 and FIG. 4. The video component includes at least one video display module (e.g., liquid crystal displays (LCD), plasma displays, projection displays, or otherwise) 301 for displaying the entertainment images. Preferably, the video component includes two display modules, one display module for each eye of the patient. The video component further includes at least one lens for each display module. Preferably, a set of optical lenses 302 focus the image for each of the patient's eyes. The video component further includes a printed circuit board (PCB) 304 in communication with the display module(s). In one specific example, a cable 305 inside the video glasses housing (e.g., housing and shielding layer) connects the LCD control electronics printed circuit board 304 to the LCDs 301. As mentioned above, A shielded cable 108 connects the LCD control electronics printed circuit board 304 to the control unit 106 (e.g., while generally maintaining the shielding layer throughout). The cable 108 provides the video data and power (e.g., DC power) for the LCD.

The video component further includes a housing 306 that may be configured in shape/profile to correspond to the patient's face. For example, the housing may include a shaped configuration so that the video glasses may be comfortably supported on the patient's face. It is appreciated that the shaped configuration of the video glasses generally correspond to the patient's face so that the LCD displays 301 and lenses 302 may be positioned juxtaposed to the eye(s) of the patient for the patient to watch video entertainment. The housing 306 of the video component (e.g., video glasses) may further include padding 314 on at least a portion of or completely along the edges of the housing to accommodate the patient's face comfortably. The padding 314 may include one or more sanitary covers 307 that may be in direct contact with the patient's face. The sanitary covers may be replaceable and/or disposable so that MRI system operators can easily replace them for different patients and/or different housings of additional (e.g., space or back-up) video components (e.g., video glasses). Desirably, the sanitary covers (e.g. pads) may reduce contamination between patients. Optionally or as an alternative, the housing may include a face mask and/or ear pads (e.g., edge portion of the video glasses and/or headphones that contact the patient such as the face and/or ears). The face mask and/or ear pads may be formed of a material (e.g., padding, foam, vinyl, leather, plastic, rubber, or otherwise) that may include anti-bacterial properties, non-allergenic properties, or otherwise and/or may be easily sanitized with wipes, such as an alcohol soak or swab.

As mentioned herein, the video component may include one or more shielding layers at least partially or completing encasing the video component. For example, the display shielding layer may include a first portion shielding layer 308 that encases the video display PCB 304 and the LCD displays 301. The housing 306 may be further configured to support the first portion of the display shielding layer 308. In one configuration, the first portion of the display shielding layer may include one or more shielding layers (e.g., one or more metal mesh screens) to encase the display module and the PCB. In a preferred embodiment, the display shielding layer(s) may further include a second portion shielding layer that at least partially or completing encases the display lenses. As mentioned herein, a mesh in front of the display of the video component may degrade the video image when viewed through the mesh. When included, the second portion of the display shielding layer includes a transparent conductive layer 309 to at least partially or completely surrounds (e.g., encases) the display lenses. A transparent conductive film across the lenses may provide increased visual quality relative to a similarly shaped mesh across a similar lens configuration and/or orientation while adequately attenuating the RF signals without producing eddy current anomalies. Transparent conductive film, with suitable ground to increase attenuation, was shown to provide an adequate RF shield. As shown in FIG. 3 the transparent conductive screen 309 generally opposes the exterior surface of the display lenses. It should be appreciated that the first and second portions of the shielding layer may be co-extensive to ensure substantial or complete encasing of the video component to substantially reduce or prevent RF signals from entering, being emitted from, or both the video component.

The video component may include two or more display shielding layers extending across the first portion of the display shielding layers, at a cable interface, or a combination of both. It is appreciated that each display shielding layer may include the metallic mesh (e.g., 100 mesh copper screen soldered together at the joints). When included, two generally opposing metallic mesh screens may be separated by the spacer layer having the insulating layer to resist any displacement that would bring the two opposing shielding layers into direct contact with each other as discussed herein as discussed herein.

The transparent conductive layer 309 may substantially reduce RF energy from entering and leaving the video component (e.g., through the display lenses) while not significantly degrading the image quality of the display module (e.g., LCD). It should be appreciated that mesh or screen material, when included as the transparent conductive layer, may be visible to the patient; therefore it may be desirable to reduce the mesh wire density across the lenses to improve visual image. Accordingly, the transparent conductive layer 309 may be included as a film transparent layer. The transparent film may include a visible transmittance of at least about 25%, preferably at least about 50%, and more preferably at least about 82%. For example, the visible transmittance of the transparent film may range from about 50% to about 95%, and preferably from about 75% to about 95%. The transparent film may also include a surface resistance less than about 80 ohms per square, and typically less than 45 ohms per square. Preferably the surface resistance may range from about 2 to about 45 ohms per square or from about 2 to about 16 ohms per square. It is believed that a calculated RF "shield effectiveness" in dB may be determined for the transparent film for a large area film of $20*\log[7e11/(\text{frequency}*R)]$ where R is the surface resistance. Furthermore, the transparent film may include a thickness (e.g., through the viewing axis such as the line of sight) that is less than about 5 mm, and preferably less than 1 mm (e.g., about 0.025 mm). Exemplary transparent conductive film material sold under the product designation AgHT-4 and AgHT-8, which are commercially available from CPFilms, Fieldale Va.

It is appreciated that the transparent film shielding layer may only provide at most about 40 dB attenuation over a large surface such as a computer monitor where the distance to metallic ground is large (e.g., at least about 12 inches). Desirably, over surfaces (e.g., small surfaces) with smaller distances (e.g., less than about 1 inch) to the metallic ground (e.g., the mesh shielding layers), the transparent film shielding may provide at least about 20 dB, and preferably at least about 40 dB (e.g., about 60 dB) attenuation over the surfaces. For example, these attenuations (e.g., at least about 20 dB, at least about 40 dB, or at least about 60 dB) over the surfaces may be achieved by a distance of less than 1 inch, and preferably less than 0.5 inch between the transparent film shielding layer and mesh shielding layer to provide sufficient grounding of the transparent film.

It should be appreciated that the transparent conductive film or otherwise shielding layer for covering the lenses may be stiff and/or easy damaged. As such, the shielding layer (e.g., transparent conductive film) may further include a protective layer (not shown) to reduce or prevent damage (e.g., scratch, tear, or otherwise) to the resistive layer. It is appreciated that the protective layer may positioned such that the transparent conductive film extends between the lens and the protective layer (e.g., in a generally adjacent arrangement). The protective layer may include a thickness (e.g., through the viewing axis such as the line of sight) of about 1.0 mm to about 10 mm, and preferably from about 1.5 mm to about 4 mm. The protective layer may be configured to include a compressive strength of at least about 50 MPa, and preferably at least about 80 MPa. Exemplary materials for the protective layer may in clued generally transparent materials including, but not limited to polycarbonate, polyethylene, polypropylene, polybutylene, or any combination thereof.

It should be appreciated that patients may not typically wear optical glasses with the MRI because the glasses may contain ferromagnetic material, such as steel screws or other material that may cause MRI artifacts and/or there may be a limited amount of space within the MRI (e.g., about 2 to about 3 inches between the patient and the MRI head coil). As such, the video component may further include an optical correction feature to correct (e.g., adjust) the focus of the image being viewed. For example, the optical correction feature may correct the focus of the image being viewed to compensate for patients with various levels of eye conditions such as Myopia, Hyperopia, Astigmatism, or otherwise, or any combination thereof.

In another embodiment, the optical correction feature may include adding a corrective lens, and adjustable corrective lens, or a replaceable corrective lens in front of each display lens (e.g., between the lens and the eye of the patient).

In a preferred embodiment, the video component may be attached to the audio component for mounting to the patient's head. For example, the video glasses may be attached to the headphones with adjustable headphone arms 312 that hold the video glasses 105 and headphones 104 on the patient's head. More particularly, the headphones may include a first earpiece and a second earpiece, each earpiece (e.g., adjustable earpiece) extending from the video glasses through a support arm 312 such that the video glasses and the headphones are mounted (e.g., secured) to the head of the patient through tension generated by the support arms of the first and second earpieces to the patient's head. The attachment of the video component to the audio component is preferred because one unit is easier for a patient to put on, and eliminates external cable between the video and audio component, which can be damaged. The attached video and audio components should fit a range of patient head sizes comfortable and provide sufficient tension to secure the visor on the patient's head and sufficient audio seal over the patient's ears. In a preferred embodiment, a single arm connects the two earphones, and attaches at the center of video component between the patient's eyes. The long length of the arm allows for a wide range of head width, while provide tension in the preferred range. However, it is appreciated that the audio component attachment (e.g., the tension generated by the support arms) may be insufficient or uncomfortable when attached to the video component or the audio component (e.g., headphones) may be separate (e.g., not attached through the support arms) from the video component (e.g., video glasses) that the video component (e.g., video glasses) may further include a mounting feature 313 such as a strap or otherwise to attach the video component to the patient's head. For example, the video glasses in include a strap (e.g., elastic strap such as found in ski goggles or masks) that holds the video glasses to the patient's face.

Headphones

The present invention includes an audio component for producing audible sound waves to a patient positioned in an MRI during the operation thereof. In a preferred embodiment, the audio component may be located in headphones 104 as shown in FIG. 3 and FIG. 4. In one embodiment the audio component (e.g., headphones) 104 may be configured to substantially attenuate the loud noise emitted from the MRI system while producing the entertainment audio sound. The audio component may include earphones housings (e.g., earpieces) 401 over each ear 403. In one configuration, the housings resemble cups, however other configurations may be used. The earphones housing 401 may include passive noise attenuation material 402 (e.g., lining the housing). Exemplary passive noise attenuation materials may include, but are not limited to insulating foam, silicone gel, or a combination of both. The passive noise attenuation material may be between about 0.25 to about 2.5 inches or about 0.5 to about 1.5 inches thick (e.g., generally along the axis of the ears).

The audio component (e.g., headphones) may include non-magnetic piezoelectric speakers capable of producing the audible sound waves of at least about 50 dBA, typically at least about 70 dBA, and more typically at least about 90 dBA. The audio component may include passive noise attenuation being capable of at least about 10 dB noise attenuation, typically at least about 15 dB noise attenuation, and more typically at least about 20 dB noise attenuation.

The audio component may further include padding 404 along the edges of the housing 401 (e.g., generally in contact with the patient's head) to reduce or resist the MRI system noise from being heard by the patient's ear, which is generally surrounded by the housing 401. In addition, the padding may be further configured to increase the comfort of the audio component (e.g., headphones) for the patient. The padding 404 may be insulating foam or, silicone gel, inside a plastic sleeve, or otherwise. It is appreciated, that the audio component may attenuate the MRI system noise by at least about 5 dB, and typically at least about 10 dB or more. Preferably the audio component may attenuate the MRI system noise from about 5 dB to about 45 DB or more preferably from about 15 dB to about to about 35 dB.

The audio component may further include speakers 406 producing audible sound waves (e.g., the entertainment system sound). Preferably, the speakers may be non-ferromagnetic. It is appreciated that the speakers may be configured to provide a sound pressure level of at least about 70 dBA, typically at least about 80 dBA, and preferably at least about 90 dBA. In one configuration, the speakers may be piezoelectric speakers. The control unit 106 generates an electrical signal for driving the audio component (e.g., the speakers 406). As discussed herein, the audio component may be in communication (e.g., attached) to the video component (e.g., video glasses) through cables 109, which preferably may be flexible cables with a shielding layer (e.g., mesh screen) to reduce or prevent RF signals from being emitted by or entering the cable 109.

The audio component may further include active noise cancellation. When included, a microphone 407 (e.g., non-ferromagnetic microphone) monitors the sound levels proximate to the patient's ear 403. The active noise cancellation system compares the monitored sound to the entertainment sound. Upon determining a difference in the monitored sound from the entertainment sound, the active noise cancellation system produces a sound to reduce of cancel the sound other than the intended entertainment sounds.

The audio component may further include one or more shielding layers. In one embodiment, the shielding layer may include a mesh screen 408 that at least partially or completely encases the speakers 406 and optionally the monitoring microphone, when included for noise cancellation 407. Preferably, the mesh screen 408 may be in close proximately to or direct contact with the shielding layer of the cable 109 to generally maintain a co-extensive shielding layer. For example, the mesh screen 408 of the headphones connects (e.g., by proximately or direct contact) to the mesh screen of the cable 109 so as to complete a portion of the Faraday shield surrounding the entertainment system. It is appreciated that the shielding layer (e.g., mesh screen 408) generally surrounds the audio component (e.g., the electronics of the headphones) to substantially reduce or prevent RF signals from entering or leaving the audio component.

In one specific configuration, the headphones include adjustable arms 312 that connect the earphone housings 401 to the video glasses housing 306. The adjustable arms 312 presses (e.g., in tension) the earphones housings 401 to the patient's head 105. The adjustable arms 312 provide sufficient pressure on the patient's head 105 for an adequate audio seal of earphones to attenuate the MRI system noise. The adjustable arms 312 support the video glasses on the patient's face, to correctly position the video glasses (e.g., lenses) in front of the patient's eyes. The patient can adjust the adjustable arms 312 to accommodate the patient's head size and comfort. It is appreciated that the adjustable arms 312 may be adjusted by moving a first portion of the adjustable arm relative to another portion. Upon moving the first and second portions to increase or decrease the distance between the video component (e.g., video glasses) and the audio component (e.g., headphones), the adjustable arms maintain the adjustment until the adjustable arms are re-adjust again. The adjustable arms may include a fastener having an engaged configuration for maintaining the adjustable arms in the adjusted position and a disengaged configuration for allowing the first and second portions to move freely relative to one another. The fastener may be a friction fit fastener, a break-away fastener, a buckle, a bolt screw, or otherwise.

Control Unit

Figure 5:
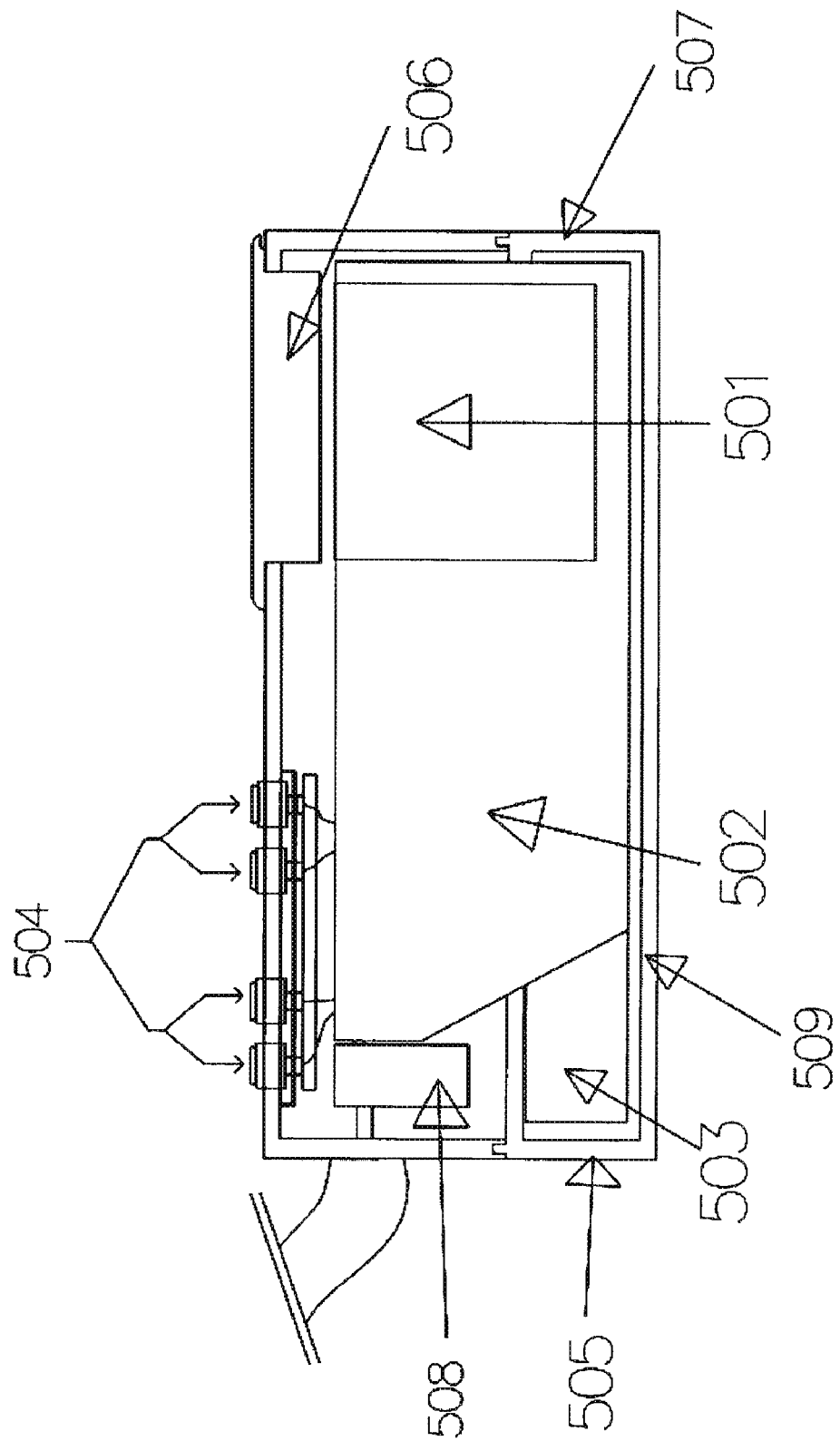
FIG. 5 is a side view of one embodiment of the control unit according to the present invention.

The present invention further includes a control unit 106 for generating electrical signals for driving the audio component, the video component, or both. As shown in FIG. 5, the control unit may include one or more of the following components: (a) an electronic storage medium, (b) a control unit printed circuit board (PCB) 502, (c) a battery 503, or any combination thereof. The control unit includes a housing 509 for support and/or securement of the components located therein.

The control unit may include an electronic storage medium for storing media for the entertainment system. The media may include one or more media types, one or more media of one or more media types, or otherwise. For example, the media may include one or more videos such as images (e.g., jpg, gif, pdf, or otherwise image formats), movies (e.g., mov, mpeg, avi, or otherwise movie formats), or otherwise and/or one or more audios such as music (e.g., MP3s, AAC, or otherwise audio formats), or otherwise, or any combination thereof. Examples of electronic storage mediums include, but are not limited to random-access memory (RAM), read-only memory (ROM), flash memory, hard drives, DVD/CD/HDVD/Blue-ray drives, media readers, or otherwise. Optionally or as an alternative, the electronic storage medium may also include removable data storage such as DVD, CD, HDVD, Blue-ray, ScanDisc, Compact Flash, MicroDrive, Smart Media Card, MultiMedia Card, Memory Stick, Secure Digital Card, Radio Frequency Identification (RFID), or otherwise. In one preferred embodiment, the electronic storage medium 501 may be a solid-state memory device (e.g. having DRAM volatile memory and/or NAND flash non-volatile memory). Preferably, the electronic storage medium is free of magnetic components and/or ferromagnetic components. It is appreciated that a combination of entertainment media (e.g., formats) and storage mediums may provide entertainment within an MRI from various techniques. In one embodiment, the MRI operator may download media from the internet (e.g., purchased from retailers such as iTunes) directly to the self-contained entertainment system (e.g., through WiFi or otherwise) and/or onto a computer, then transfer the media to a memory card. Thereafter, the media is ready for playing in the self-contained entertainment system. It is appreciated that the electronic storage medium may be included elsewhere, other than or in addition to the control unit. For example, the storage medium may be included in the video component (e.g., video glasses), the audio component (e.g., headphones), or otherwise or may be by itself. It should be contemplated that the electronic storage may be located outside of the MRI (e.g., in the MRI control room or otherwise) and wirelessly connected to the entertainment system as discussed below.

In one specific example, the electronic storage medium is a media card reader for receiving a solid state media card (e.g., memory card) so that to change the media (e.g., entertainment), an operator opens the card door 506 of the control unit 106 (e.g., preferably outside of the magnet room), removes the existing memory card and installs another memory card, typically having different media stored therein. It is appreciated that the card door 506 may be accessible through a portion of the control unit housing 509.

The control unit further includes a video PCB 502. The video PCB 502 reads the media from the electronic storage medium 501 and generates the electrical signals (e.g., a video signal and/or an audio signal) for driving the video component (e.g., video glasses 103) and/or audio component (e.g., headphones 104), respectively.

The control unit may further include at least one amplifier and/or at least one low pass filter. When included, the amplifier and/or low pass RF filter may be positioned about a circuit board 508 for generating the function(s) of the amplifier and/or low pass filter. For example, in one configuration, the circuit board 508 (e.g., amplifier) may increase the amplitude of the electrical signals (e.g., video and audio signals) sufficiently for acceptable operation (e.g., about 1 volt to about 6 volts (e.g. about 3 volts) peak-to-peak voltage to speaker to produce an audio amplitude of about 60 dBA to about 120 dBA (e.g. about 90 dBA or about 110 dBA)) of the audio component (e.g., headphones 104). In another configuration, the circuit board 508 (e.g., low-pass filter) may reduce RF energy by more than about 10 dB from entering and/or leaving the control unit 106.

The control unit may further include at least one power source 503 for supplying power (e.g., DC power) to one or more components of the entertainment system. One example of a power source may be a battery. The power source may be regenerative (e.g., rechargeable) removable, non-removable, or any combination thereof. In a preferred embodiment, the power source may be a rechargeable battery. The power source 503 may be configured with sufficient capacity to power the entertainment system for a time longer than the typical MRI session (e.g., the time a patient is in an MRI system). It is appreciated that the capacity of the power source to power the entertainment system may be sufficient for a time of at least at least 1 hour, at least 2 hours, at least 5 hours, at least 8 hours, at least 10 hours, at least 20 hours or more during the operation of the MRI system. Examples of rechargeable power sources include, but are not limited to rechargeable alkaline battery (alkaline), nickel cadmium batteries (NiCd), nickel hydrogen batteries (NIH2), nickel metal hydride batteries (NiMH), lithium ion batteries (Li-ion), and lithium ion polymer batteries (Li-ion polymer), fuel cells, or otherwise. In one preferred embodiment the power source may be a battery with at least 5,000 mA-hours at 3.7 V so that the capacity to power the entertainment system may be greater than about 8 hours or more and fits within the control unit 106. It should also be appreciated that the power source 503 may be included elsewhere, other than or in addition to the control unit. For example, the power source may be included in the video component (e.g., video glasses), the audio component (e.g., headphones), or otherwise or may be by itself. It was contemplated that a large RF pulse may heat the battery and/or discharge the battery, however proper shielding of the battery as discussed herein provided safe use of the battery in an MRI during the operation thereof.

It is appreciated that the control unit housing 509 may include a power source door 507 for accessing and/or removing the power source 503. In one specific example, once the rechargeable battery charge is low, the MRI system operator opens the battery door 507 to remove the low-battery (e.g., while outside the MRI magnet room). The MRI system operator removes the low-battery 503 and may replace the low-battery with a charged battery. It is appreciated that the entertainment system may further include a charger for recharging the power source. As such, the MRI system operator may put the low-battery (e.g., the battery with a lower charge) in a battery charging station.

The control unit 106 may further include a user interface so that the operator may control (e.g., communicate with) the entertainment system. The user interface may include one or more activators (e.g., buttons, switches, transducers, devices that respond to a voice comment or any combination thereof) for communicating with the control unit by the patient. The one or more activators having one or more preset conditions that may include selecting a media type (e.g., video such as a movie or audio such as music), selecting media to be played from a compilation of individual medias, playing media (e.g., viewing an image or video, listening to audio), fast forwarding media, rewinding media, browsing media, stopping or pausing playback of media; audio adjustment (increasing volume or decreasing volume), video adjustment (brightness, contrast), or any combinations thereof.

The user interface may be further configured such that the activators may be different in shape and/or size for recognition from touch by the user. For example, the activators may be physically recognizable by the patient's fingers and/or thumb. The activators may be from about 2 to about 8 mm (e.g., about 5 mm) wide. The activators may be opposing one another by spacing from about 2 to about 8 mm (e.g., about 5 mm) of separation. Desirably, the activators 504 may be provided in a generally simple configuration for rapid learning by the patient so that minimal or no intervention by the MRI system operator staff may be required. It is appreciated that upon activation of an activator (e.g., selecting one or more of the preset conditions) by the user, the control unit generates corresponding electrical signals for driving the video component, the audio component, or both thereby providing direct feedback (e.g., operation of the entertainment system) to the patient.

The control unit further includes a housing 509 and one or more shielding layers as discussed herein. The housing unit may be configured to support the shielding layer while at least partially or completely enclosing the control unit from the surrounding environment. In one embodiment, the shielding layer 505 may include a mesh screen that at least partially or completely encases the control unit (e.g., the electronics of the control unit) and the user interface, when included. Preferably, the mesh screen may be in close proximately to or direct contact with the shielding layer of the cable 108 (that connects the control unit to the video component) to generally maintain a co-extensive shielding layer. The shielding layer may be generally pliable (e.g., flexible) so that control (e.g., operation) of the entertainment system through the user interface (e.g., by activation of the activators) may be generally maintained without compromising the integrity of the shielding layer surrounding the activators of the user interface during activation thereof. It is appreciated that upon closing the electric storage medium door 506 and/or the power source door 507, when included, a seal may be formed to complete a portion of the shielding layer (e.g., Faraday shield) surrounding the entertainment system. It is appreciated that the shielding layer 505 (e.g., mesh screen) of the control unit housing 509 and optionally the electric storage medium door 506 and/or the power source door 507, when included, generally surrounds the control unit (e.g., the electronics of the control unit) to substantially reduce or prevent RF signals from entering or leaving the control unit.

In a preferred embodiment, the shielding layer of the door (e.g., mesh screen) electrically contacts the shielding layer of the control unit (e.g., mesh screen) along all edges of the door. The RF electrical resistance between the door shield and the control unit shield is less than 0.1 ohms in the frequency range of about 1 MHz to 150 MHz. There is a large physical overlap of the two shields to make a tortuous RF path which keep RF leakage from the door to a very low level. The physical overlap of the contacting shield is from about 0.25 cm to about 5 cm, with a preferred overlap of about 1 cm. In a preferred embodiment, the door locks the control unit with sufficient pressure to make low resistance RF contact between the door shield and the control unit shield. In the preferred embodiment, there is a compliment material under the door shield, or under the control unit shield, or under both shields, which allows one or both shield to deform slightly and form a strong electrical contact or a large area of the overlapping shields.

The control should allow the physical movement of the electrical control buttons without allowing RF leakage. In a preferred embodiment, a patient presses mechanical buttons on the outside of the control unit, and these mechanical buttons press on the electrical buttons inside the shield chassis of the control unit. The control unit shielding over the electrical buttons should both be flexible and electrically continuous. In a preferred embodiment, the shield around the control unit chassis goes through the holes in the chassis for the mechanical buttons and electrically contacts one or more shielding layers over the electrical buttons, which are inside the chassis. The chassis is the plastic structure, which contains all the electronics of the control unit.

The control unit 106 may be configured in shape and/or size to be mounted on the patient. Preferably, the control unit may be configured in shape and/or size to be held within the hand of the patient as shown in FIG. 1. In this configuration, the movement of the patient may be reduced (e.g., minimized) within the magnet bore of the MRI system.

Figure 6:
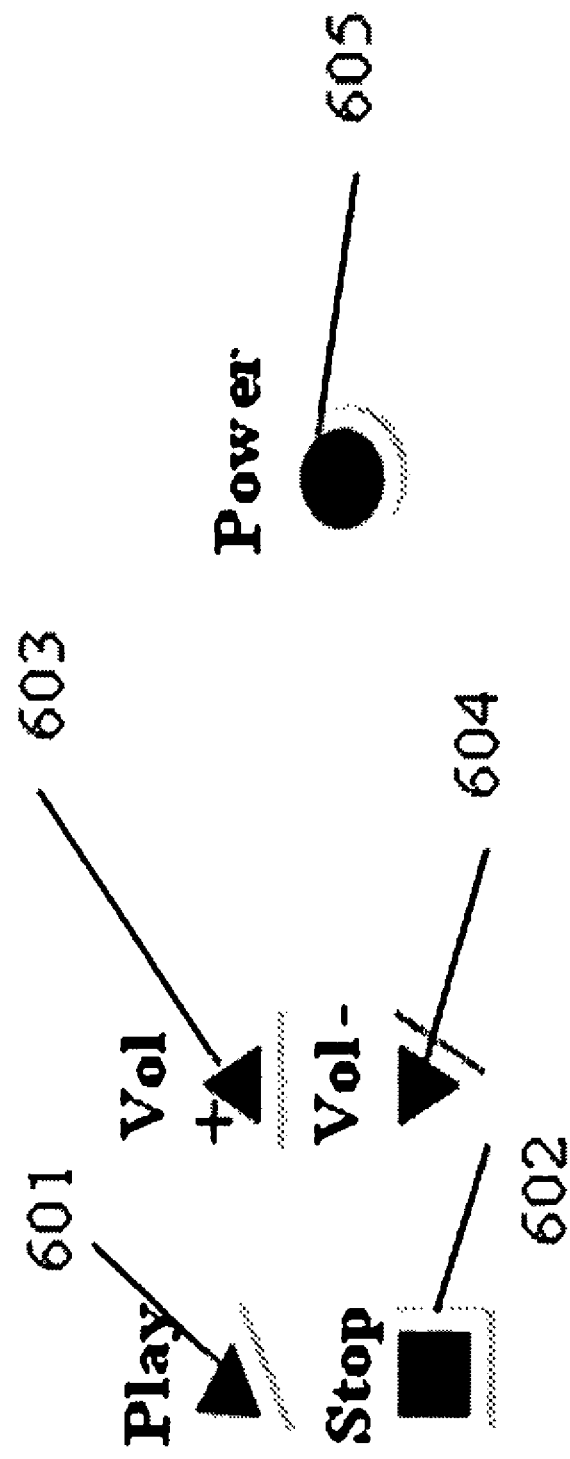
FIG. 6 is a top view of one embodiment of the user interface according to the present invention.

FIG. 6 shows an example of controls on the user control module. The controls illustrated include a play button 601, a stop butto 602, an up volume button 603, a down volume button 604 and a power button 605.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The preferred embodiment of the present invention has been disclosed. A person of ordinary skill in the art would realize however, that certain modifications would come within the teachings of this invention. Therefore, the following claims should be studied to determine the true scope and content of the invention.

The invention claimed is:

1. An entertainment system for use with by a patient in a magnetic resonance imaging (MRI) device comprising:
   a. an audio component for producing audible sound waves from an electrical signal;
   b. a video component for producing a video image from an electrical signal;
   c. a control unit configured to generate the electrical signal for driving the audio component, the video component, or both, the control unit including:
      (i) an electronic storage medium, wherein the electrical signal is generated from media stored in the electronic storage medium, the electronic storage medium being free of magnetic components or ferromagnetic components;
      (ii) a battery for providing power to the audio component, the video component, and the control unit; and
      (iii) one or more shielding layers at least partially encapsulating the control unit to reduce or prevent RF signals from entering, being emitted from, or both the control unit;
   d. one or more cables extending from the control unit and battery to the audio component and the video component for electronic communication and providing power therebetween, the one or more cables including a shielding layer to reduce or prevent RF signals from entering, being emitted from, or both the one or more cables;
   wherein the system includes less than about 20 grams by weight of ferromagnetic material per Tesla of the MRI;
   wherein the shielding layers comprise about 2 to about 5 layers of conductive metal mesh which includes a network of elongated wires that define a plurality of openings therethrough having between 15 and 200 wires per inch; and
   wherein the control unit may be disposed within a magnetic bore of the MRI device during the operation thereof;
   wherein the cable allows control unit and battery to be placed outside the MRI imaging area during operation thereof to reduce MRI imaging anomalies.

2. The system of claim 1, wherein the video component includes a video display for displaying a video image of the electrical signal, at least one lens for focusing the video image for one or both eyes of the patient, and one or more shielding layers at least partially encapsulating the video component to reduce or prevent RF signals from entering, being emitted from, or both the video component.

3. The system of claim 1, wherein the one or more shielding layers of the control unit, the video component, or both includes at least two generally opposing conductive meshes separated by a spacer layer that resists any displacement that would bring the two opposing meshes into direct contact with each other.

4. An entertainment system for use with by a patient in a magnetic resonance imaging (MRI) device comprising:
   a. an audio component for producing audible sound waves from an electrical signal;
   b. a video component for producing a video image from an electrical signal;
   c. a control unit configured to generate the electrical signal for driving the audio component, the video component, or both, the control unit including:

(i) an electronic storage medium, wherein the electrical signal generated from media stored in the electronic storage medium, the electronic storage medium being free of magnetic components or ferromagnetic components;

(ii) a power source for providing power to the audio component, the video component, and the control unit; and (iii) one or more shielding layers at least partially encapsulating the control unit to reduce or prevent RF signals from entering, being emitted from, or both the control unit;

d. one or more cables extending from the control unit to the audio component and the video component for electronic communication and providing power therebetween, the one or more cables including a shielding layer to reduce or prevent RF signals from entering, being emitted from, or both the one or more cables;

wherein the system includes less than about 20 grams by weight of ferromagnetic material per Tesla of the MRI;

wherein the control unit may be disposed within a magnetic bore of the MRI device during the operation thereof;

wherein the video component includes a video display for displaying a video image of the electric signal, at least one lens for focusing the video image for one or both eyes of the patient, and one or more shielding layers at least partially encapsulating the video component to reduce or prevent RF signals from entering, being emitted from, or both the video component wherein the or more shielding layers of the control unit, the video component or both includes at least two generally opposing non-magnetic meshes separated by a spacer layer that resists any displacement that would bring the two opposing meshes into direct contact with each other;

wherein the spacer layer includes an insulating layer having a dielectric strength of at least about 500 volts.

5. The system of claim 1, wherein the control unit comprises a housing wherein the housing is encased with one of the shielding layers, and one or more doors for changing, or recharging, the power source and changing the entertainment by replacing media or uploading data, wherein the one or more doors comprise one or more of the shielding layers, wherein the shielding layers of the housing unit and the one or more doors surround the control unit and the shielding of the one or more doors and the control unit overlap by at least 0.25 cm complete around the opening in the control unit for the door and make electrical contact with an RF resistance of less than 0.1 ohm.

6. An entertainment system, for use with by a patient in a magnetic resonance imaging (MRI) device comprising:

a. an audio component for producing audible sound waves from an electrical signal;

b. a video component for producing a video image from an electrical signal;

c. a control unit configured to generate the electrical signal for driving the audio component, the video component, or both, the control unit including:

(i) an electronic storage medium, wherein the electrical signal is generated from media stored in the electronic storage medium, the electronic storage medium being free of magnetic components or ferromagnetic components, (ii) a power source for providing power to the audio component, the video component, and the control unit; and (iii) one or more shielding layers at least partially encapsulating the control unit to reduce or prevent RF signals from entering, being emitted from, or both the control unit;

d. one or more cables extending from the control unit to the audio component and the video component for electronic communication and providing power therebetween, the one or more cables including a shielding layer to reduce or prevent RF signals from entering, being emitted from, or both the one or more cables;

wherein the system includes less than about 20 grams by weight of ferromagnetic material per Tesla of the MRI;

wherein the control unit may be disposed within a magnetic bore of MRI device during the operation thereof;

wherein the video component includes a video display for displaying a video image of the electric signal, at least one lens for focusing the video image for one or both eyes of the patient, and one or more shielding layers at least partially encapsulating the video component to reduce or prevent RF signals from entering, being emitted from, or both the video component wherein the one or more shielding layers of the control unit, the video component, or both includes at least two generally opposing non-magnetic meshes separated by a spacer layer that resists any displacement that would bring the two opposing meshes into direct contact with each other;

wherein the one or more shielding layers of the video component further includes a transparent conductive film at least partially covering the at least one lens to reduce the formation of eddy currents, to increase RF shielding, or both while providing a visual transmittance between about 75% and about 95% and a surface resistance between about 2 and about 16 ohms per square.

7. The system of claim 6, wherein the at least one lens further includes a transparent protective layer covering the transparent film, the protective layer (e.g., polycarbonate) having a compression strength of at least about 50 MPa.

8. The system of claim 1, wherein the control unit further includes the user interface and the one or more activators include an on activator, and off activator, a play activator, a pause activator, a volume adjustment activator, or any combination thereof for operation of the system by the patient during the operation of the MRI while located in the MRI bore.

9. The system of claim 1, wherein the electronic stage medium includes a solid-state storage device.

10. The system of claim 1, wherein the control unit further includes a controller board for controlling the operation of the video component, the audio component, the electronic storage medium, the user interface, and the power source, the controller board having at least one non-ferromagnetic inductor to reduce or prevent RF signals from being transmitted from the power source and along the one or more cables.

11. The system of claim 3, wherein the video glasses and the control unit further include a generally solid housing, each housing having a first portion formed of a conductive or resistive material and a second portion formed of the one or more shielding layers so that the first portion at least partially surrounds the second portion.

12. A method for media playback using a self-contained entertainment system within a magnetic resonance imaging (MRI) device during the operation thereof comprising the steps of:

providing the self contained entertainment system according to claim 1 mounting the video glasses and the headphones to the head of a patient through tension generated by the support arms of the first and second earpieces such that the at least one lens generally oppose one or both eyes of the patient and each earpiece is generally disposed over an ear of the patent;

positioning at least a portion of the patient within a magnetic bore of the MRI such that the self-contained entertainment system is located therein;

selecting one or more conditions of the user interface; and generating electrical signals by the control unit based on the selected one or more conditions for driving the video component, the audio component, or both;

wherein the self-contained entertainment system is worn by the patient inside the magnet bore of the MRI during the operation of both the system and the MRI.

13. The system of claim 1 wherein the one or more cables extending from the control unit to the audio component and the video component have a length of from about 1 to about 15 feet.

14. The system of claim 1 wherein the shield surrounds the control unit including a storage medium door and power source door and the audio electronics and the video component are inside conductive shields and shielded cables connect the control unit, audio component and video component.

15. The system of claim 1 wherein the ratio of grams of magnetic material in the system to the magnetic field of the MRI bore in Tesla is 15:1 or less.

16. The system of claim 14 wherein the shielding layer completely encases the control unit and is in direct contact with the shielding of the one or more cables extending from the control unit to the audio component and the video component.

17. The system of claim 1 wherein the control unit comprises a housing and at least a shielding layer integrated into the housing.

18. The system of claim 8 wherein the activators comprise a mechanical button on the outside of the control units and a corresponding electrical button inside of the control unit wherein a shielding layer is disposed between each corresponding electrical button and mechanical button wherein the shielding layer is flexible and electrically continuous.

19. The system of claim 18 wherein the shielding layer on the housing comprises a patterned conductive layer on the surface of the housing.

20. The system of claim 1, wherein the conductive shielding comprises a conductive mesh printed onto one or more of the system components.

* * * * *